United States Patent
Buchanan et al.

(10) Patent No.: US 7,759,524 B2
(45) Date of Patent: Jul. 20, 2010

(54) PROCESS FOR PRODUCING PHENOL AND METHYL ETHYL KETONE

(75) Inventors: John Scott Buchanan, Lambertville, NJ (US); Jihad Mohammed Dakka, Whitehouse Station, NJ (US); Stephen Zushma, Clinton, NJ (US); Francisco Manuel Benitez, Houston, TX (US); Steven E. Silverberg, Seabrook, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 12/317,044

(22) Filed: Dec. 18, 2008

(65) Prior Publication Data
US 2009/0216048 A1    Aug. 27, 2009

Related U.S. Application Data

(60) Provisional application No. 61/008,988, filed on Dec. 21, 2007.

(51) Int. Cl.
*C07C 45/53* (2006.01)
*C07C 37/08* (2006.01)
(52) U.S. Cl. .................. 568/385; 568/716; 568/754
(58) Field of Classification Search ............... 568/385, 568/716, 754
See application file for complete search history.

(56) References Cited

U.S. PATENT DOCUMENTS

| 5,059,736 | A | * | 10/1991 | Tamura et al. ............. 585/461 |
| 5,210,354 | A | | 5/1993 | Dubner et al. |
| 5,298,667 | A | | 3/1994 | Iwanaga et al. |
| 7,282,613 | B2 | | 10/2007 | Black et al. |
| 2007/0118006 | A1 | | 5/2007 | Vaporciyan |

FOREIGN PATENT DOCUMENTS

| EP | 1088809 | 8/2000 |
| JP | 56131529 A | 10/1981 |
| WO | WO 2007/143239 A2 | 12/2007 |

OTHER PUBLICATIONS

Process Economics Report No. 22B, "Phenol", p. 113-122, 261-263, Stanford Research Institute, Dec. 1977.

* cited by examiner

*Primary Examiner*—Sikarl A Witherspoon
(74) *Attorney, Agent, or Firm*—Robert A. Migliorini

(57) ABSTRACT

In a process for producing phenol and methyl ethyl ketone, benzene and a $C_4$ olefin are contacted under alkylation conditions and in the presence of an alkylation catalyst to produce sec-butylbenzene. The sec-butylbenzene is then oxidized to produce an oxidation effluent comprising sec-butylbenzene hydroperoxide and acetophenone. At least part of the sec-butylbenzene hydroperoxide in the oxidation effluent is cleaved to produce phenol and methyl ethyl ketone, while at least part of the acetophenone is hydrogenated to produce at least one of methyl benzyl alcohol, styrene and ethylbenzene.

16 Claims, 3 Drawing Sheets

US 7,759,524 B2

PROCESS FOR PRODUCING PHENOL AND METHYL ETHYL KETONE

CROSS-REFERENCE TO RELATED APPLICATIONS

This is a Non-Provisional Application that claims priority to U.S. Provisional Application 61/008,988 filed Dec. 21, 2007, which is herein incorporated by reference.

FIELD

The present disclosure relates to a process for co-producing phenol and methyl ethyl ketone.

BACKGROUND

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and co-produces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-122 and 261-263 of Process Economics Report No. 22B entitled "Phenol", published by the Stanford Research Institute in December 1977.

It is also known that a mixture of phenol with varying quantities of methyl ethyl ketone and acetone can be produced by oxidizing a feed containing cumene and sec-butylbenzene and then cleaving the resultant hydroperoxides. By controlling the weight ratio of cumene to sec-butylbenzene in the feed, the ratio of acetone to methyl ethyl ketone in the product can be varied depending on market conditions. See European Published Application No. 1,088,809 and U.S. Pat. No. 7,282,613.

However, the production of phenol using sec-butylbenzene as one or the alkylbenzene precursor is accompanied by certain problems which either are not present or are less severe with a cumene-based process. For example, in comparison to cumene, oxidation of sec-butylbenzene to the corresponding hydroperoxide is very slow in the absence of a catalyst and is very sensitive to the presence of impurities. Moreover, in cumene oxidation, the major by-product is dimethyl benzyl alcohol, which is readily dehydrated to alpha-methyl styrene and hydrogenated back to cumene for recycle to the process. However, in the case of sec-butylbenzene oxidation, it is found that a significant by-product is acetophenone even when the oxidation is conducted in the presence of a catalyst, such as N-hydroxyphthalimide. Since the market for acetophenone is limited, its production could adversely impact process economics. The present disclosure seeks to address this problem by providing an integrated process for producing phenol and methyl ethyl ketone, either alone or in combination with acetone, in which the by-product acetophenone is converted to higher value products.

SUMMARY

In one aspect, the disclosure resides in a process for producing phenol and methyl ethyl ketone, the process comprising:

(a) contacting benzene and a $C_4$ olefin under alkylation conditions and in the presence of an alkylation catalyst to produce sec-butylbenzene;

(b) oxidizing the sec-butylbenzene from (a) to produce an oxidation effluent comprising sec-butylbenzene hydroperoxide and acetophenone;

(c) cleaving at least part of the sec-butylbenzene hydroperoxide in said oxidation effluent to produce phenol and methyl ethyl ketone; and (d) hydrogenating at least part of the acetophenone in said oxidation effluent to produce at least one of methyl benzyl alcohol, styrene and ethylbenzene.

In one embodiment, the hydrogenating (d) is conducted after the cleaving (c).

Conveniently, the process further comprises (e) separating at least part of the phenol and methyl ethyl ketone from said oxidation effluent. In one embodiment, the separating (e) comprises removing from the oxidation effluent a fraction boiling at to below the boiling point of phenol.

Generally, the hydrogenating (d) is conducted after the separating (e). In one embodiment, the hydrogenating (d) is conducted on the entire oxidation effluent remaining after the separating (e).

Conveniently, the hydrogenating (d) converts at least part of the acetophenone in said oxidation effluent to methyl benzyl alcohol. In one embodiment, the process further comprises dehydrating at least part of the methyl benzyl alcohol to styrene. In a further embodiment, the process further comprises (g) hydrogenating at least part of the styrene to ethylbenzene.

Alternatively, the hydrogenating (d) converts at least part of the acetophenone in said oxidation effluent directly to styrene.

As a further alternative, the hydrogenating (d) can convert at least part of the acetophenone in said oxidation effluent directly to ethylbenzene.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE EMBODIMENTS

Figure 1:
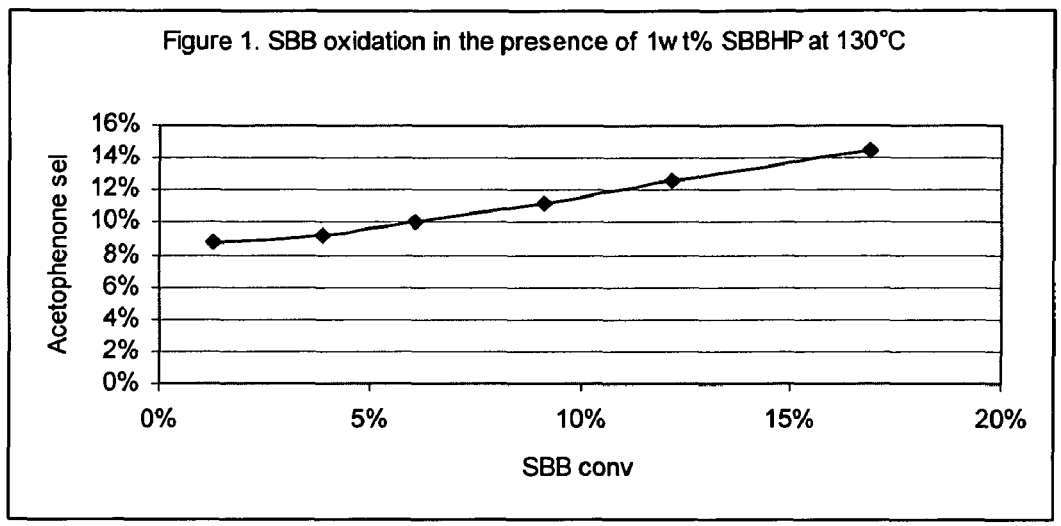
FIG. 1 is a graph of acetophenone selectivity against sec-butylbenzene conversion in the uncatalyzed air oxidation of sec-butylbenzene at 130° C. according to the process of Example 1.

Described herein is a process for producing phenol and methyl ethyl ketone. In the process, sec-butylbenzene is produced by alkylating benzene with a $C_4$ olefin and the resultant sec-butylbenzene is oxidized to produce an oxidation effluent comprising sec-butylbenzene hydroperoxide and acetophenone as a by-product. The sec-butylbenzene hydroperoxide in the oxidation effluent is then cleaved to produce phenol and methyl ethyl ketone, whereas the by-product acetophenone is hydrogenated to produce at least one of methyl benzyl alcohol, styrene and ethylbenzene. The methyl benzyl alcohol can then be dehydrated to produce styrene, which can be recovered as a useful product or can be hydrogenated to produce ethylbenzene. All numerical values within the detailed description and the claims herein are understood as modified by "about."

Sec-Butylbenzene Production

The sec-butylbenzene production step in the present process is effected by alkylating benzene with at least one $C_4$ olefin under alkylation conditions in the presence of a heterogeneous catalyst. The alkylation conditions conveniently include a temperature of from 60° C. to 260° C., for example between 100° C. and 200° C. The alkylation pressure is conveniently 7000 kPa or less, for example from 1000 to 3500 kPa. The alkylation is conveniently carried out at a weight hourly space velocity (WHSV) based on $C_4$ olefin of between 0.1 and 50 $hr^{-1}$, for example between 1 and 10 $hr^{-1}$.

The $C_4$ olefin conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table 1 below.

TABLE 1

| | | Raffinate 1 | | Raffinate 2 | |
|---|---|---|---|---|---|
| Component | Crude $C_4$ stream | Solvent Extraction | Hydrogenation | Solvent Extraction | Hydrogenation |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| | |
|---|---|
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

$C_4$ hydrocarbon fractions obtained from the conversion of oxygenates, such as methanol, to lower olefins more typically have the following composition:

| | |
|---|---|
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above $C_4$ hydrocarbon mixtures can be used in the alkylation process. In addition to linear butenes and butanes, these mixtures typically contain components, such as isobutene and butadiene, which can be deleterious to the alkylation process. For example, the normal alkylation product of isobutene with benzene is tert-butylbenzene which, as previously stated, acts as an inhibitor to the subsequent oxidation step. Thus, prior to the alkylation step, these mixtures may be subjected to butadiene removal and isobutene removal. For example, isobutene can be removed by selective dimerization or reaction with methanol to produce MTBE, whereas butadiene can be removed by extraction or selective hydrogenation to butene-1. Conveniently, the $C_4$ alkylating agent employed in the present process contains less than 1.5 wt %, advantageously less than 0.5 wt %, isobutene and less than 0.1 wt % butadiene.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Conveniently, the total feed to the alkylation step of the present process contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

It is also possible to employ a mixture of a $C_4$ olefin, as described above, and $C_3$ olefin, such as propylene, as the alkylating agent in the present alkylation process so that the alkylation step produces a mixture of cumene and sec-butylbenzene. The resultant mixture can then be processed through oxidation and cleavage, to make a mixture of acetone and MEK, along with phenol, advantageously where the molar ratio of acetone to phenol is 0.5:1, to match the demand for bisphenol-A production. Typically, where the alkylating agent is a mixture of a $C_4$ olefin and $C_3$ olefin, the $C_3$ olefin is present in an amount between 1 wt % and 80 wt % of the olefin mixture.

The alkylation catalyst used in the alkylation process is conveniently a crystalline molecular sieve of the MCM-22 family. The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, advantageously one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Advantageously, the molecular sieve is selected from (a) MCM-49, (b) MCM-56 and (c) isotypes of MCM-49 and MCM-56, such as ITQ-2.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic used in the synthesis mixture from remaining in the zeolite crystals as vapor phase crystallization occurs.

Prior to use in the alkylation process, the MCM-22 family zeolite, either in bound or unbound form, may be contacted with water, either in liquid or vapor form, under conditions to improve its sec-butylbenzene selectivity. Although the conditions of the water contacting are not closely controlled, improvement in sec-butylbenzene selectivity can generally be achieved by contacting the zeolite with water at temperature of at least 0° C., such as from 10° C. to 50° C., for a time of at least 0.5 hour, for example for a time of 2 hours to 24 hours. Typically, the water contacting is conducted so as to increase the weight of the catalyst by 30 to 75 wt % based on the initial weight of the zeolite.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen. Advantageously, the reactants are at least partially in the liquid phase.

Using an MCM-22 family zeolite as the catalyst and butene-1, butene-2 or a mixture thereof as the $C_4$ olefin, the alkylation process produces at least 90%, normally at least 95%, of sec-butylbenzene by weight of the alkylated product. Although the alkylation step is highly selective towards sec-butylbenzene, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite.

The transalkylation reaction is typically conducted under at least partial liquid phase conditions, which suitably include a temperature of 100 to 300° C., a pressure of 1000 to 7000 kPa, a weight hourly space velocity of 1 to 50 hr$^{-1}$ on total feed, and a benzene/polyalkylated benzene weight ratio of 1 to 10.

Sec-Butyl Benzene Oxidation

Oxidation of the sec-butylbenzene is conveniently accomplished by contacting the alkylation product, generally after separation of the unreacted benzene, with an oxygen-containing gas, such as air, in the liquid phase and normally in the presence of a catalyst. Thus, unlike cumene, atmospheric air oxidation of sec-butylbenzene in the absence of a catalyst is very difficult to achieve. For example, at 110° C. and at atmospheric pressure, sec-butylbenzene is not oxidized, while cumene oxidizes very well under the same conditions. At higher temperature, the rate of atmospheric air oxidation of sec-butylbenzene improves; however, higher temperatures also produce significant levels of undesired by-products.

Suitable sec-butylbenzene oxidation catalysts include a water-soluble chelate compound in which multidentate ligands are coordinated to at least one metal from cobalt, nickel, manganese, copper, and iron (See U.S. Pat. No. 4,013,725). More advantageously, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Advantageously, the catalyst is N-hydroxyphthalimide. Another suitable catalyst is N,N',N"-thihydroxyisocyanuric acid.

These catalysts can be used either alone or in the presence of a free radical initiator and can be used as liquid-phase, homogeneous catalysts or can be supported on a solid carrier to provide a heterogeneous catalyst. Where the oxidation feed comprises a mixture of cumene and sec-butylbenzene, the oxidation step can be effected in the absence of a catalyst, although again improved conversion and selectivity to the hydroperoxides are achieved in the presence of one or more of the catalyst listed above.

Suitable conditions for the sec-butylbenzene oxidation step include a temperature between 70° C. and 200° C., such as 90° C. to 130° C., and a pressure of 0.5 to 20 atmospheres (50 to 2000 kPa). A basic buffering agent, such as sodium carbonate, may be added to react with acidic by-products that may form during the oxidation. In addition, an aqueous phase may be introduced, which can help dissolve the basic buffering agent. The per-pass conversion in the oxidation step is advantageously kept below 50%, to minimize the formation of byproducts. The oxidation reaction is conveniently conducted in a catalytic distillation unit.

The oxidation step converts the sec-butylbenzene to sec-butylbenzene hydroperoxide, but also produces significant quantities of acetophenone, generally at least 1% by weight of sec-butylbenzene converted, probably as a result of beta-scission of an ethyl group from the sec-butylbenzene during the oxidation process. Thus the effluent from the oxidation process generally comprises from 5 wt % to 40 wt % sec-butylbenzene hydroperoxide, from 1 wt % to 20 wt % acetophenone, from 1 wt % to 10 wt % 2-phenyl-2-butanol and the remainder unreacted sec-butylbenzene. The sec-butylbenzene hydroperoxide produced is generally concentrated by distilling off the unreacted sec-butylbenzene prior to the cleavage step. The unreacted sec-butylbenzene can then be recycled to the oxidation step.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of 20° C. to 150° C., such as 40° C. to 120° C., a pressure of 50 to 2500 kPa, such as 100 to 1000 kPa and a liquid hourly space velocity (LHSV) based on the hydroperoxide of 0.1 to 100 hr$^{-1}$, advantageously 1 to 50 hr$^{-1}$. The sec-butylbenzene hydroperoxide is advantageously diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

Acetophenone Removal and Upgrading

As indicated above, the oxidation of sec-butylbenzene tends to produce significant quantities of acetophenone and hence the present process provides for upgrading the acetophenone to higher value products. Another impurity frequently produced in the oxidation step is 2-phenyl-2-butanol and in one embodiment the present process also provides for the conversion of the 2-phenyl-2-butanol to sec-butylbenzene for recycling to the oxidation step.

Conveniently, the acetophenone is upgraded by initially hydrogenating the acetophenone to methyl benzyl alcohol (MBA), which can then be dehydrated to styrene. The styrene can be recovered as a saleable product or further hydrogenated to produce ethylbenzene.

Suitable conditions for hydrogenation of acetophenone to methyl benzyl alcohol include a temperature of 20° C. to 500° C., such as 90° C. to 155° C., a pressure of 15 psig to 2000 psig (200 kPa to 13900 kPa), such as 1200 psig (8375 kPa), and H$_2$/acetophenone molar ratio of 2:1 to 8:1. The hydrogenation is generally conducted in the presence of a catalyst comprising one or more elements or compounds thereof from Groups 4 to 14, especially Groups 6 to 12 of the Periodic Table, which may be supported on porous support. Suitable catalysts include copper/zinc oxide, zinc oxide on barium-copper chromite, copper chromium and Rh—Sn/alumina.

Dehydration of the resultant methyl benzyl alcohol to styrene can be conducted in the vapor phase at a temperature of 25° C. to 300° C., such as 180° C. to 280° C., and a pressure at or below atmospheric pressure in presence of catalysts such as $TiO_2$, silica, alumina, and silicoaluminates. However, this regime leads to coking, requiring frequent regeneration of the catalyst.

An alternative process for converting the methyl benzyl alcohol to styrene, in which the coking problem is mitigated, involves effecting the dehydration in the liquid phase, in the presence of an acid catalyst. Suitable acid catalysts include mineral acids (e.g. sulfuric, phosphoric), organo-sulfonic acids (e.g. p-toluene sulfonic acid), carboxylic acids (e.g. phthalic anhydride), cation exchange resins, and acidic metal or mixed metal oxides, such as high surface area aluminas, aluminum silicates, and zeolites. Suitable conditions include a temperature of 50° C. to 280° C., with sufficient pressure, at or below atmospheric pressure, to maintain at least partial liquid phase. Product styrene may exit the reactor overhead as a vapor.

Hydrogenation of the styrene to ethylbenzene can readily be accomplished at a temperature of 20° C. to 300° C., such as 50° C. to 200° C., a pressure of 170 kPa to 13900 kPa, and $H_2$/styrene molar ratio of 1:1 to 8:1, generally in the presence of a catalyst comprising one or more elements or compounds thereof from Groups 6 to 12 of the Periodic Table, and advantageously supported on porous carrier.

In another embodiment, the acetophenone is upgraded in a single step hydrogenation/dehydration/hydrogenation process directly to ethylbenzene. Suitable conditions for such a process include a temperature of 50° C. to 400° C., a pressure of 170 kPa to 13900 kPa (10 to 2000 psig), and $H_2$/acetophenone molar ratio of 1:1 to 8:1. Suitable catalysts include elements or compounds thereof from Groups 4 to 14, especially Groups 6 to 12 of the Periodic Table, which may be supported on porous support. The catalysts may advantageously incorporate an acidic component, such as an alumina, aluminosilicate, or zeolite, to promote dehydration of any intermediate alcohol formed. Although the process may result in some oversaturation of the ethylbenzene to ethylcyclohexane, for certain applications the presence of small quantities of ethylcyclohexane can be tolerated. For the example, the blending research octane number of ethylcyclohexane is 43, as compared with 124 for ethylbenzene, so that a few percent ethylcyclohexane in the product should still give a high octane blend stock. Both compounds are well-established gasoline blending components.

Irrespective of the method employed, upgrading of the acetophenone can be effected by removing the acetophenone from the oxidation effluent before the sec-butylbenzene hydroperoxide is sent to the cleavage step, and then treating the acetophenone as described above. More typically, however, the acetophenone to be upgraded is removed from the effluent produced in the cleavage step. In either case, removal of the acetophenone is typically achieved by distillation.

Alternatively, the effluent from the cleavage step can be fractionated to remove the methyl ethyl ketone and phenol, typically by removing the fraction boiling at to below the boiling point of phenol (182° C. at atmospheric pressure) and the entire heavy ends stream from the distillation step can then be hydrogenated to upgrade the acetophenone in the stream. In this case, there may be a heavy boiling tail that needs to be eliminated, e.g. by distillation, after hydrogenation. As a further alternative, an extra-heavy ends (tar) may be split off from the heavy ends and sent to fuel, and a stream boiling in the 38 to 260° C. (100 to 500° F.) normal boiling point range could be routed through the hydrogenation reactor. Advantageously, this pre-splitting of the feed to the hydrogenation reactor is accomplished in an existing MEK/phenol process vacuum distillation tower, e.g. by pulling a side-draw rich in acetophenone, while letting the tar go to the tower bottom. In this case, no further removal of a heavy tail should be needed after hydrogenation, saving on number of distillation towers.

In one practical embodiment of the alternative described in the preceding paragraph, the cleavage effluent is distilled to remove the fraction boiling at to below the boiling point of phenol, and the remaining effluent is subjected to a single step hydrogenation/dehydration/hydrogenation process as described above. In this way, not only can the acetophenone in the cleavage effluent be converted directly to ethylbenzene, but also any 2-phenyl-2-butanol produced as an impurity in the oxidation step can be converted back to sec-butylbenzene. The product can then be distilled to remove a low boiling point, ethylbenzene fraction and an intermediate boiling point sec-butylbenzene fraction from the remaining heavy ends and the sec-butylbenzene can be recycled to the oxidation step.

As a further alternative, the effluent from the cleavage step can be fractionated to remove the methyl ethyl ketone and phenol and to separate a $C_8$ oxygenate fraction composed mainly of acetophenone. The $C_8$ oxygenate fraction, with or without prior hydrogenation to convert part of the acetophenone to methyl benzyl alcohol (MBA), can then be fed to the MBA dehydration unit of a propylene oxide/styrene plant. Thus in a propylene oxide/styrene plant, ethylbenzene is oxidized to produce ethylbenzene hydroperoxide, which is then epoxidized with propylene to produce propylene oxide and MBA, together with a small amount of acetophenone impurity. Since the acetophenone level is low, the $C_8$ oxygenate product from the epoxidation step is fed directly to an MBA dehydration unit to convert the MBA to styrene. The acetophenone impurity is then removed from the styrene product and hydrogenated to produce additional MBA, which can then be recycled to the dehydration step. By feeding the acetophenone-rich $C_8$ oxygenate fraction from the sec-butylbenzene hydroperoxide cleavage step to the MBA dehydration unit of a propylene oxide/styrene plant, the need for a separate acetophenone treatment unit in the plant for converting sec-butylbenzene to phenol and methyl ethyl ketone can be avoided.

The disclosure will now be more particularly described with reference to the following non-limiting Examples and the accompanying drawings.

EXAMPLES

Example 1

Oxidation of Sec-Butylbenzene

Sec-butylbenzene (150 gr) was weighed into a 300 ml Parr Reactor fitted with a stirrer, thermocouple, gas inlet, sampling port and a condenser containing a Dean Stark type adapter for water removal. The reactor and content was stirred at 700 rpm and sparged with nitrogen at a flow rate of 250 cc/min for five minutes. The reactor was pressurized with nitrogen to 100 psig (791 kPa) and while maintaining a nitrogen sparge the reactor was heated to the desired temperature (130° C.). When the reaction temperature was reached the gas was switched from nitrogen to air and the reactor was sparged with air at the desired flow rate for six hours. Samples were taken hourly. After six hours the gas was switched back to nitrogen and the heat was turned off. When the reactor had cooled, the reactor was depressurized and the contents removed. A graph of the acetophenone selectivity against sec-butylbenzene conversion is shown in FIG. 1, from which it will be seen that, in the absence of a catalyst, the acetophenone selectivity was 15% at a sec-butylbenzene conversion level of 17%.

Example 2

Oxidation of Sec-Butylbenzene in the Presence of NHPI

Figure 2:
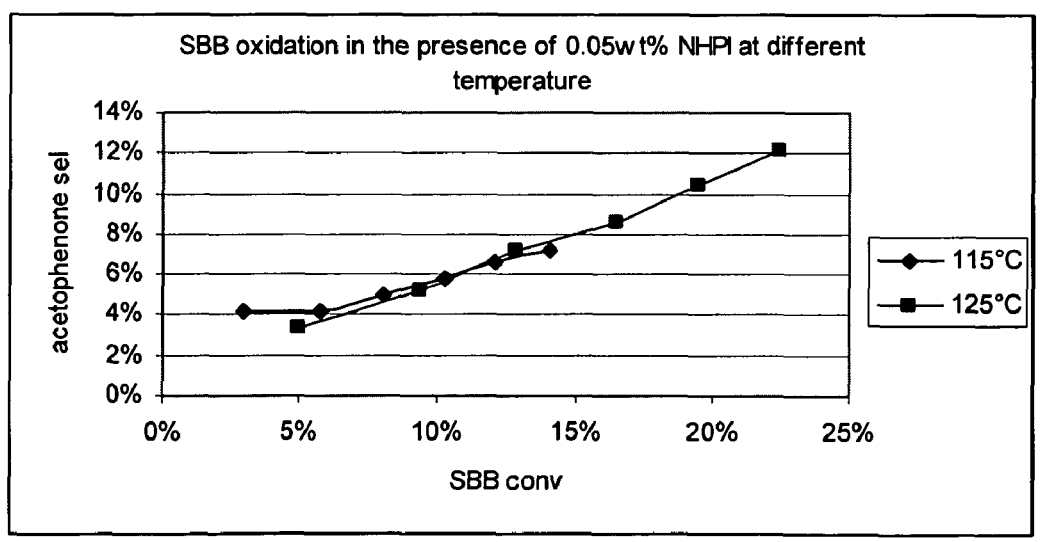
FIG. 2 is a graph of acetophenone selectivity against sec-butylbenzene conversion in the air oxidation of sec-butylbenzene in the presence of 0.05 wt % of N-hydroxyphthalimide at 115° C. and 125° C. according to the process of Example 2.
Figure 3:
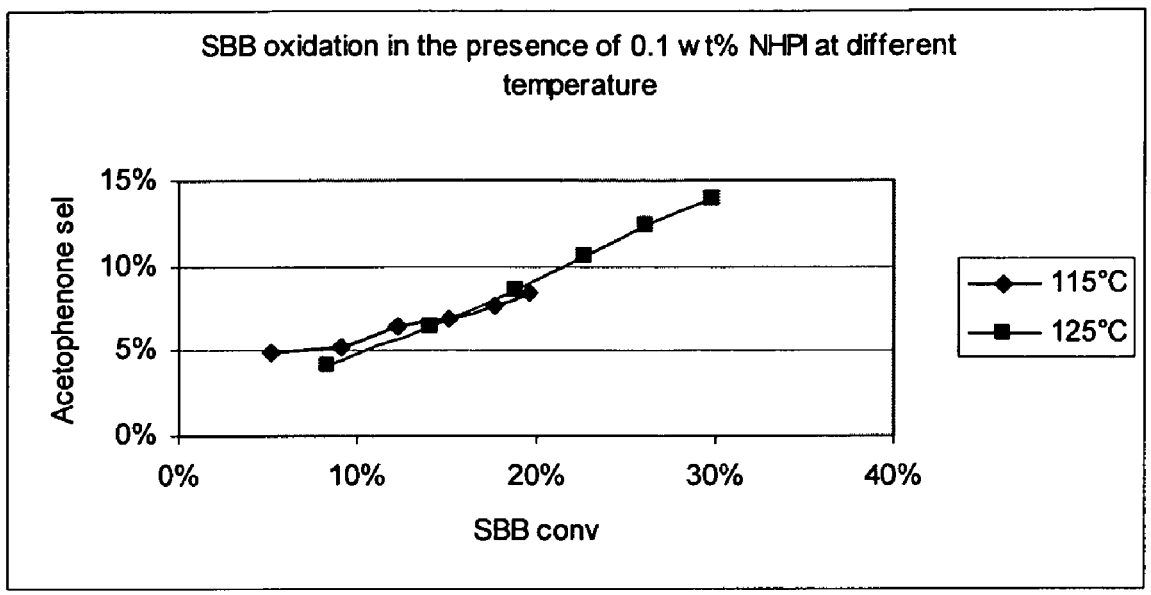
FIG. 3 is a graph of acetophenone selectivity against sec-butylbenzene conversion in the air oxidation of sec-butylbenzene in the presence of 0.1 wt % of N-hydroxyphthalimide at 115° C. and 125° C. according to the process of Example 2.
Figure 4:
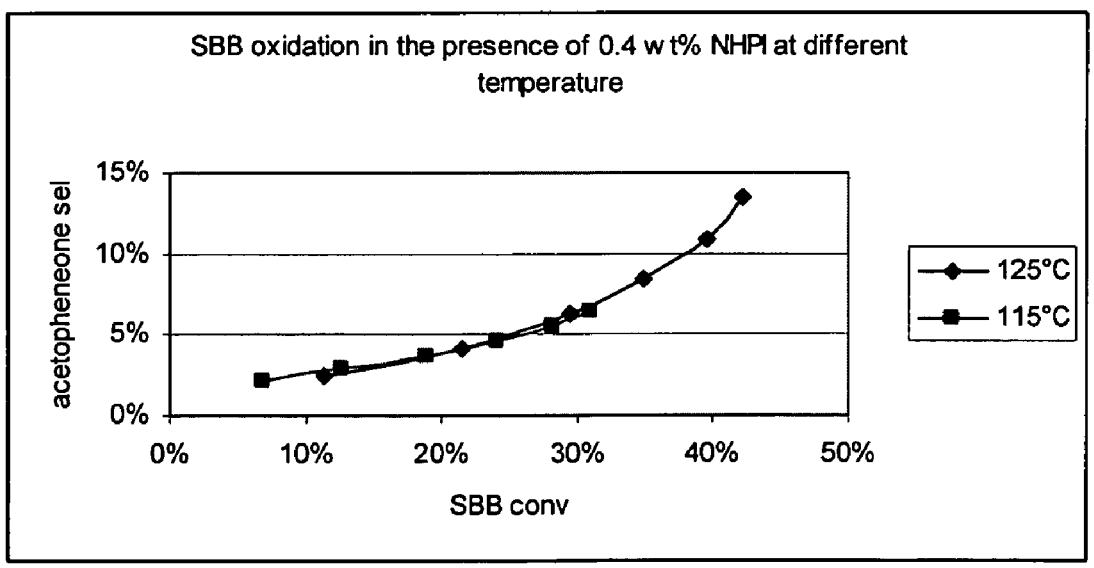
FIG. 4 is a graph of acetophenone selectivity against sec-butylbenzene conversion in the air oxidation of sec-butylbenzene in the presence of 0.4 wt % of N-hydroxyphthalimide at 115° C. and 125° C. according to the process of Example 2.

Sec-butylbenzene (150 gr) and different amounts (0.05 wt %, 0.1 wt %, 0.43 wt %) of N-hydroxyphthalimide (NHPI) were weighed into a 300 ml Parr Reactor fitted with a stirrer, thermocouple, gas inlet, sampling port and a condenser containing a Dean Stark type adapter for water removal. The reactor and content was stirred at 700 rpm and sparged with nitrogen at a flow rate of 250 cc/min for five minutes. The reactor was pressurized with nitrogen to 100 psig (791 kPa) and while maintaining a nitrogen sparge the reactor was heated to the desired temperature (115 or 125° C.). When the reaction temperature was reached the gas was switched from nitrogen to air and the reactor was sparged with air at the desired flow rate for six hours. Samples were taken hourly. After six hours the gas was switched back to nitrogen and the heat was turned off. When the reactor had cooled the reactor was depressurized and the contents removed. FIGS. 2 to 4 are graphs plotting the acetophenone selectivity against sec-butylbenzene conversion at the different temperatures and the different NHPI concentrations. The data show that, temperature and NHPI concentration affect the acetophenone selectivity.

Example 3

Oxidation of Mixture of Cumene and Sec-Butylbenzene

A mixture of sec-butylbenzene (116.3 gr) and cumene (33.6 gr) was weighed into a 300 ml Parr reactor fitted with a stirrer, thermocouple, gas inlet, sampling port and a condenser containing a Dean Stark type adapter for water removal. The reactor and content was stirred at 700 rpm and sparged with nitrogen at a flow rate of 250 cc/min for five minutes. The reactor was pressurized with nitrogen to 100 psig (791 kPa) and while maintaining a nitrogen sparge the reactor was heated to the desired temperature (130° C.). When the reaction temperature was reached the gas was switched from nitrogen to air and the reactor was sparged with air at the desired flow rate for six hours. Samples were taken hourly. After six hours the gas was switched back to nitrogen and the heat was turned off. When the reactor had cooled the reactor was depressurized and the contents removed.

Figure 5:
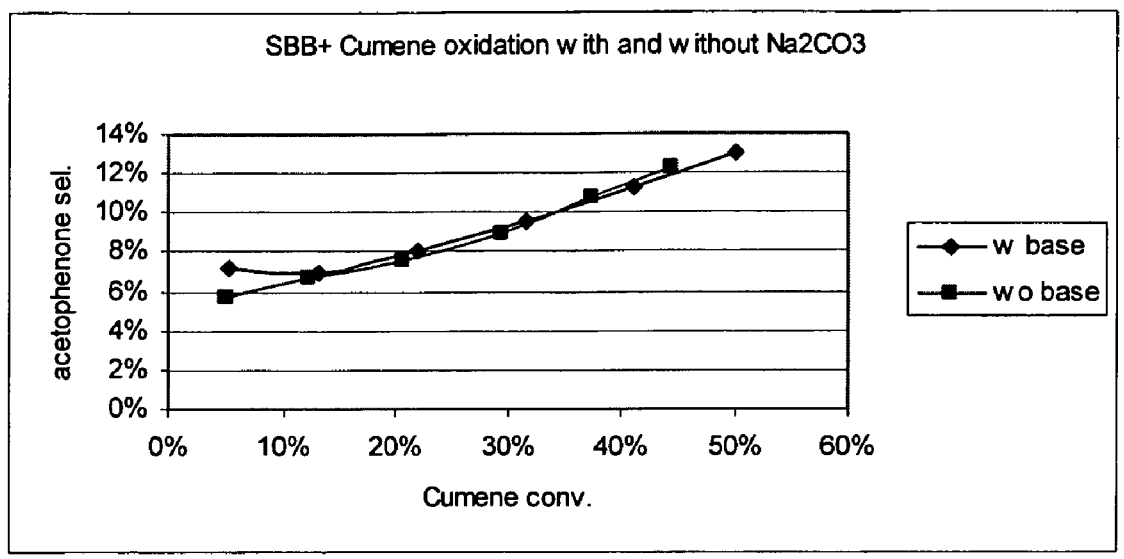
FIG. 5 is a graph of acetophenone selectivity against cumene conversion in the uncatalyzed air oxidation of a mixture of cumene and sec-butylbenzene at 130° C., with and without the addition of sodium carbonate, according to the process of Example 3.
Figure 6:
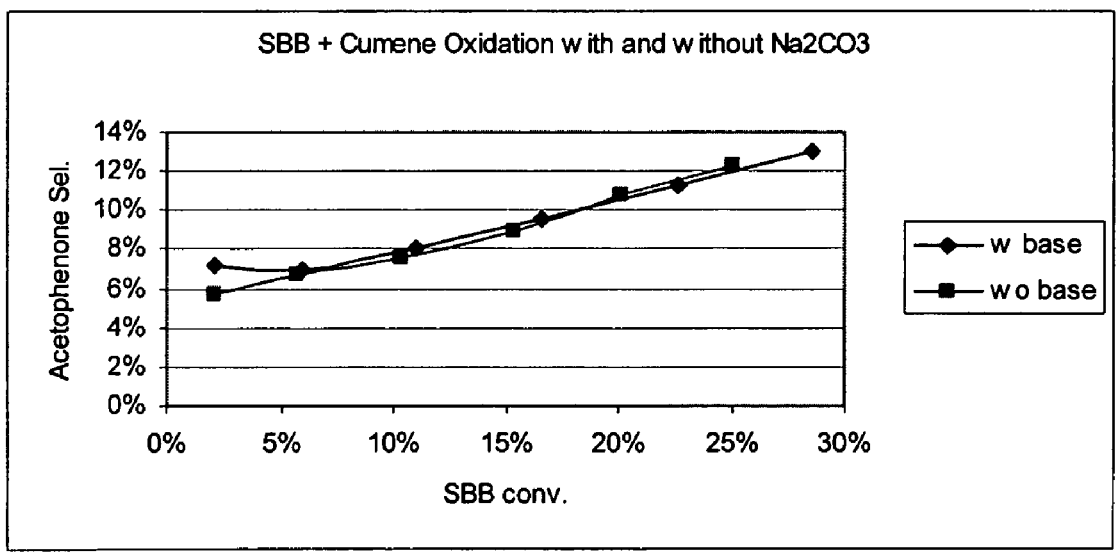
FIG. 6 is a graph of acetophenone selectivity against sec-butylbenzene conversion in the uncatalyzed air oxidation of a mixture of cumene and sec-butylbenzene at 130° C., with and without the addition of sodium carbonate, according to the process of Example 3.

The above procedure was repeated but with $Na_2CO_3$ (0.15 gr) and distilled water (0.48 gr) being weighed into the Parr Reactor together with the mixture of sec-butylbenzene (116.3 gr) and cumene (33.6 gr). FIGS. 5 and 6 compare the cumene and sec-butylbenzene reactions respectively both with and without the addition of the base. The data show that addition of base improves the conversion but that similar acetophenone selectivity profiles are obtained irrespective of base addition.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

What is claimed is:

1. A process for producing phenol and methyl ethyl ketone, the process comprising:
   (a) contacting benzene and a $C_4$ olefin under alkylation conditions and in the presence of an alkylation catalyst to produce sec-butylbenzene;
   (b) oxidizing the sec-butylbenzene from (a) to produce an oxidation effluent comprising see-butylbenzene hydroperoxide and acetophenone;
   (c) cleaving at least part of the sec-butylbenzene hydroperoxide in said oxidation effluent to produce phenol and methyl ethyl ketone; and
   (d) hydrogenating and dehydrating in a single step at least part of the acetophenone in said oxidation effluent to produce at least one of methyl benzyl alcohol, styrene and ethylbenzenc using a hydrogenation and dehydration catalyst comprising a hydrogenation function and a dehydration function, wherein the hydrogenation and dehydration catalyst includes a metal from Groups 4 to 14 of the Periodic Table of Elements or a compound thereof.

2. The process of claim 1, wherein the hydrogenating and dehydrating (d) is conducted after the cleaving (c).

3. The process of claim 2 and further comprising:
   (e) separating at least part of the phenol and methyl ethyl ketone from said oxidation effluent.

4. The process of claim 3, wherein the separating (e) comprises removing from the oxidation effluent a fraction boiling at to below the boiling point of phenol.

5. The process of claim 3, wherein the hydrogenating and dehydrating (d) is conducted on a portion of said oxidation effluent remaining after the separating (c).

6. The process of claim 3, wherein the hydrogenating and dehydrating (d) is conducted on the entire oxidation effluent remaining after the separating (e).

7. The process of claim 1, wherein the hydrogenation and dehydration catalyst includes a metal from Groups 6 to 12 of the Periodic Table of Elements or a compound thereof.

8. The process of claim 3 and further comprising:
   (f[h]) hydrogenating at least part of the styrene to ethylbenzene.

9. The process of claim 8, wherein the hydrogenating (f) is conducted in the presence of a catalyst comprising a metal from Groups 6 to 12 of the Periodic Table of Elements or a compound thereof.

10. The process of claim 1, wherein the hydrogenating and dehydrating (d) converts at least part of the acetophenone in said oxidation effluent directly to cthylbenzene.

11. The process of claim 10, wherein the hydrogenating and dehydrating (d) is conducted in the presence of a catalyst comprising a metal from Groups 6 to 12 of the Periodic Table of Elements or a compound thereof.

12. The process of claim 10, wherein the oxidation effluent also comprises 2-phenyl-2-butanol and the hydrogenating and dehydrating (d) converts at least part of the 2-phenyl-2-butanol to seccbutylbenzene.

13. The process of claim 12 and comprising recycling at least part of the sec-butylbenzene produced by the hydrogenating and dehydrating (d) to the oxidizing (b).

14. The process of claim 1, wherein at least part of the oxidation effluent is combined with a methyl benzene alcohol stream from a propylene oxide/styrene plant and the combined stream is dehydrated to convert methyl benzene alcohol to styrene.

15. The process of claim 14 wherein said hydrogenating and dehydrating (d) is conducted prior to combining at least part of the oxidation effluent with said methyl benzene alcohol stream.

16. The process of claim 14 wherein said hydrogenating and dehydrating (d) is conducted on at least part of the acetophenone contained in said combined stream after the combined stream is dehydrated to convert methyl benzene alcohol to styrene.

* * * * *